United States Patent
Dündar et al.

(10) Patent No.: US 12,207,879 B2
(45) Date of Patent: Jan. 28, 2025

(54) CONTACT LENS EMBEDDED SENSOR SYSTEM FOR MONITORING CHANGES IN INTRAOCULAR PRESSURE AND METHOD FOR IMPLEMENTING THE SAME

(71) Applicant: Glakolens Biyomedikal Biyoteknoloji Tic. VE SAN. A.S., Sariyer/Istanbul (TR)

(72) Inventors: Günhan Dündar, Sariyer/Istanbul (TR); Arda Deniz Yalçinkaya, Sariyer/Istanbul (TR); Hamdi Torun, Sariyer/Istanbul (TR); Onur Ateş, Sariyer/Istanbul (TR); Ümmühan Aybüke Calikoğlu, Sariyer/Istanbul (TR); Özgür Kaya, Sariyer/Istanbul (TR); Halil Kerim Yildirim, Sariyer/Istanbul (TR)

(73) Assignee: GLAKOLENS BIYOMEDIKAL BIYOTEKNOLOJI TIC. VE SAN. A.S., Sariyer/Istanbul (TR)

( * ) Notice: Subject to any disclaimer, the term of this patent is extended or adjusted under 35 U.S.C. 154(b) by 1012 days.

(21) Appl. No.: 17/270,801

(22) PCT Filed: Aug. 23, 2018

(86) PCT No.: PCT/TR2018/050444
§ 371 (c)(1),
(2) Date: Feb. 23, 2021

(87) PCT Pub. No.: WO2020/040709
PCT Pub. Date: Feb. 27, 2020

(65) Prior Publication Data
US 2021/0393126 A1    Dec. 23, 2021

(51) Int. Cl.
*A61B 3/16*    (2006.01)
*A61B 5/00*    (2006.01)

(52) U.S. Cl.
CPC .............. *A61B 3/16* (2013.01); *A61B 5/0002* (2013.01); *A61B 2562/0261* (2013.01)

(58) Field of Classification Search
CPC . A61B 3/16; A61B 5/0002; A61B 2562/0261; H01P 1/2005; H01P 7/082;
(Continued)

(56) References Cited

U.S. PATENT DOCUMENTS 4,160,971 A * 7/1979 Jones .................... G01L 19/086
340/505
8,437,075 B2    5/2013 Baik et al.
(Continued)

FOREIGN PATENT DOCUMENTS

EP    2 412 305 A1    2/2012
EP    2 317 912 B1    11/2015
(Continued)

OTHER PUBLICATIONS

Lin et al. Novel silicone hydrogel based on PDMS and PEGMA for contact lens application, Colloids and Surfaces B: Biointerfaces, vol. 123, 2014, pp. 986-994, ISSN 0927-7765 (Year: 2014).*
(Continued)

*Primary Examiner* — Rene T Towa
*Assistant Examiner* — Justin Xu
(74) *Attorney, Agent, or Firm* — Crowell & Moring LLP

(57) ABSTRACT

A contact lens embedded sensor comprises resonator rings, characterized in that said resonator rings result from arrangements of broadside-coupled split-ring resonator, edge-coupled split-ring resonator, non-bianisotropic split-ring resonator and spiral resonator based structures with the use of dielectric, biocompatible substrate layers. The system also includes an antenna coupled with the sensor, and an electrical readout circuitry collecting and processing measurements in the change of resonant character caused by
(Continued)

intraocular pressure (IOP) perturbing the geometry of the human eyeball said contact lens is worn thereon.

12 Claims, 13 Drawing Sheets

(58) Field of Classification Search
CPC ........ G02F 1/218; G02F 1/21; G02F 2203/13; G02F 2202/30; H01Q 15/0026; H01Q 15/0086
See application file for complete search history.

(56) References Cited

U.S. PATENT DOCUMENTS

| | | | |
|---|---|---|---|
| 2011/0150030 A1* | 6/2011 | Abdelmoneum | G01K 7/32 333/219 |
| 2011/0184271 A1 | 7/2011 | Veciana et al. | |
| 2013/0225968 A1* | 8/2013 | Auvray | A61B 3/16 600/398 |
| 2014/0275936 A1* | 9/2014 | Huang | A61B 3/16 600/398 |
| 2014/0296688 A1* | 10/2014 | Lam | A61B 3/107 600/405 |
| 2017/0164878 A1* | 6/2017 | Connor | G09B 19/00 |
| 2017/0292920 A1 | 10/2017 | Torun et al. | |
| 2018/0042479 A1 | 2/2018 | Yalcinkaya et al. | |
| 2019/0298234 A1* | 10/2019 | Omenetto | G01N 27/028 |

FOREIGN PATENT DOCUMENTS

| | | |
|---|---|---|
| WO | WO 2008/083719 A1 | 7/2008 |
| WO | WO 2013/050073 A1 | 4/2013 |

OTHER PUBLICATIONS

Heath, J. (Apr. 10, 2017). Phase locked loop: a fundamental building block in wireless technology. Analog IC Tips. Retrieved May 17, 2024, from https://www.analogictips.com/faq-phase-locked-loop-pll/ (Year: 2017).*

International Search Report, issued in International Patent Application No. PCT/TR2018/050444, European Patent Office, Rijswijk, The Netherlands, dated May 8, 2019, 3 pgs.

PCT International Preliminary Report on Patentability, issued in International Patent Applicatioin No. PCT/TR2018/050444, European Patent Office, Munich, Germany, dated Feb. 3, 2020, pp. 22.

* cited by examiner

CONTACT LENS EMBEDDED SENSOR SYSTEM FOR MONITORING CHANGES IN INTRAOCULAR PRESSURE AND METHOD FOR IMPLEMENTING THE SAME

RELATED APPLICATIONS

The present patent document is a 371 of PCT Application Serial No. PCT/TR2018/050444, filed Aug. 23, 2018, designating the United States and published in English, which is hereby incorporated by reference.

TECHNICAL FIELD

The contact lense embedded sensor system disclosed hereby generally concerns a contact lens-embedded glaucoma monitoring system, related to a continuously operating, non-invasive, passive sensor built within biocompatible substrates of a contact lense, and configured to monitor levels of intraocular pressure (IOP), which may be embodied, for example, with bioprosthetics and biocompatible materials.

BACKGROUND

Ocular hypertension is the presence of the physiological condition of elevated intraocular pressure (IOP). The ciliary body in the posterior chamber of the eye produces the fluid "aqueous humour". The produced aqueous humour flows through the iris into the anterior chamber of the eye; and it is drained through the trabecular meshwork into the blood stream. If the drainage through the trabecular meshwork cannot keep up with the aqueous humour production, IOP starts to increase.

Glaucoma (open-angle) is a general denotation of a family of ocular disorders among whose common diagnosis lays ocular hypertension associated optic neuropathy. As the most prominent risk factor of glaucoma, ocular hypertension is observable with regular, organized measurements of intraocular pressure (IOP). The presence of ocular hypertension (high IOP) over extended periods may lead to optic nerve damage and permanent loss of vision in some cases (glaucoma).

SUMMARY

To address these health concerns various solutions have been proposed with varying degrees of technical depth and rigor. Publication number WO2013050073 (A1) and the family members of disclose an intraocular pressure monitoring device that allows continuous monitoring over a period of time. The IOP monitoring device comprising a soft contact lens made of such as silicone and a diaphragm-based pressure sensor. The pressure sensor comprises active strain gauges for signal transduction. It is characterized in that the active strain gauge comprises a polygonal portion and is located around the centre of the contact lens and is not in direct contact with the eye. The output of the strain gauges is transmitted using inductively coupled transmitters. The pressure sensor described above is electrically active, requiring significant amount of power to be supplied to IOP monitoring device, which is placed on eye. Besides, heat caused by a high radiation level near the patient's eye needs to be dissipated. Moreover, the electrical signal should be transmitted to a microcontroller using wireless data transmission. The fabrication of the lens is complicated and expensive.

Another document denoted with the publication number EP 2412305 (A1) discloses passive sensing means for a contact lens used in a physiological parameter measuring system, e.g. intraocular pressure (IOP), comprising one or two contact lenses, wherein each contact lens comprises an antenna and a purely passive sensing means. Physiological parameters can be measured based on the shift of the resonance frequency of an LC circuit over its deformation, obtained from computed complex impedance seen at the antenna. Purely passive sensing means described in the patent consists of spires on both sides of one flexible carrier substrate, wherein said spires are connected using a multitude of vias. The presence of an integrated arc-shaped capacitor is arranged towards the outside of the spires. The sensor further comprises at least one interdigitated capacitor, in particular connected to the capacitor. Sensing means described therein comprises spires which are connected with each other using a multitude of vias, an integrated arc-shaped capacitor and an interdigitated capacitor connected to the capacitor.

Publication number US 2011/0184271 (A1), discloses a truncated contact lens whose truncation plane is parallel to the base of said contact lens, and a polymeric nanocomposite material centrally disposed and attached to the perimeter of the truncated area, said material being sensitive to pressure changes, biocompatible and transparent, and including contact electrodes, and in that it also comprises means for transmitting IOP measurement data to an external system. The sensor disclosed in this application measures IOP changes indirectly by the changes in the resistance of the polymeric nanocomposite material included thereon through deformation. IOP measurement data can be transmitted via either wires or an integrated circuit and antenna wherein said antenna can be in the truncated lens or as a bonding element with the polymer nanocomposite material.

Publication number US 2017/0292920 (A1) discloses a biosensor that enables the concentration of a desired molecule inside a liquid in the medium, comprising at least one metallic plate functions as a ground plate at least one dielectric substrate which is located on top of the metallic plate at least one split-ring resonator which is realized on top of the dielectric substrate, and which is coated with a dielectric layer, at least two symmetrical antennas which are realized on the same plane with said split-ring resonator on the substrate.

U.S. Pat. No. 8,437,075 (B2) discloses a metamaterial structure comprising a substrate and at least a first resonator and a second resonator disposed on different surfaces of the substrate or on different layers of the substrate, wherein each of the first and second resonators is a split-ring resonator having at least one gap and wherein the first and second resonators have resonance characteristics different from each other. The disclosed metamaterial structure, further comprising electrodes that are electrically connected to the resonators. The structure disclosed herein comprises split-ring resonators which have different resonance characteristics.

Publication No: US 2018/0042479 (A1) discloses a split-ring resonator-based strain sensor multiplicity designed for glaucoma detection application. The geometry of the disclosed sensor is optimized such that it can be embedded in a conventional contact lens. Silver conductive paint is used to form the sensors realized on flexible substrates made of cellulose acetate and latex rubber. The devices are excited using a pair of monopole antennas. The disclosed sensors comprise one split-ring resonator realized on one surface of a flexible substrate made of either cellulose acetate or latex rubber. The sensor structures disclosed in this article is different from the inventive sensor in terms of structure and materials as the inventive sensor comprises more than one split-ring with flexible, substrate between them.

The contact lens embedded sensor system may provide a non-invasive IOP change monitoring system that incorporates a contact lens structure, therefore enabling continuous measuring capability all the while retaining visual capabilities of the patient to their full extent. The system may achieve such with the use of a passive sensor, i.e. lacking active components, such as comprising a metallic resonator element embedded into biocompatible dielectric substrate structures to be incorporated in the form of a contact lens, antennas and a electronic readout circuitry receiving circumferential change/bend data for corneal curvature translated to ring resonance, measurements thereof to be evaluated regarding intraocular pressure (IOP) change.

The contact lens embedded sensor system is operable on the premise that, changes in intraocular pressure (IOP) induces change in the geometry of the eyeball of a person. If the change of ocular geometry can be quantized and evaluated, it makes detection and monitoring of IOP (an etiological factor of ocular hypertension and glaucoma) possible. The IOP information can be used to monitor ocular hypertension and glaucoma, and to facilitate their management. To attain said goal, the contact lens embedded sensor system may be operable in a non-invasive manner in the form of a wearable contact lens, comprising a biocompatible passive sensor. The biocompatible passive sensor further comprising a split-ring resonator (SRR), widely utilized in microwave and radio frequency (RF) applications, with a structure of a circular/rectangular ring with a narrow gap, that is situated on a spherically deformed, reduced-length flexible substrate sensitive to deformations and perturbations on the eyeball surface of a human eyeball due to changes in IOP.

The contact lens may include/house a passive biocompatible split-ring resonator (SRR) sensor. Split-ring resonators (SRR) are particular in that, an excitation resulting from an electromagnetic radiation source causes them to mimic the behavior of resistive/inductive/capacitive (RLC) circuits. Thus when the contact lens-embedded biocompatible sensor is exposed to electromagnetic radiation (EMR), a current is induced on the conductive surface thereon, oscillating at the same frequency of the electromagnetic radiation. On the occasion that the geometry of the conductive surface supports the oscillatory motion, the biocompatible sensor operates at resonance. According to another embodiment said split-ring resonators are also available in alternative design formulations, among them edge-coupled versions with two concentric rings of different radii.

The contact lens embedded sensor system may have a sensing system-including electronic readout circuitry and antenna formations aside from aforementioned biocompatible sensors. An oscillator-based readout circuit may be employed for the purpose of resonance frequency measurement, with similar setups for one-port or two-port antenna configurations. The one-port or two-port antenna configurations comprising an antenna-coupled SRR sensor, a frequency divider and a processor circuitry, such as a microcontroller unit (MCU) for frequency counting. The resonant frequency of the antenna coupled SRR sensor may determine the oscillation frequency of the oscillator circuitry. A change in IOP may cause a shift in the resonant frequency of the sensor, which in turn may cause a shift in the frequency of the oscillator output signal. The output signal frequency of the oscillator is divided or down-converted by a frequency divider or a mixer, which may render output frequency measurable by a frequency counter or processor circuitry, such as a micro controller unit (MCU). The processor circuitry, such as a micro-controller, may transmit, or store measured intraocular pressure (IOP) information. The change between the resonance frequency versus intraocular pressure (IOP) can be measured by the scheme described herein.

BRIEF DESCRIPTION OF THE FIGURES

The accompanying drawings are given solely for the purpose of exemplifying a contact lens-embedded biocompatible sensor system for glaucoma monitoring, whose advantages were outlined above and will be explained in brief hereinafter.

The drawings are not meant to delimit the scope of protection as identified herein nor should they be referred to alone in an effort to interpret the scope identified in said claims without recourse to the technical disclosure herein.

DETAILED DESCRIPTION

Figure 1:
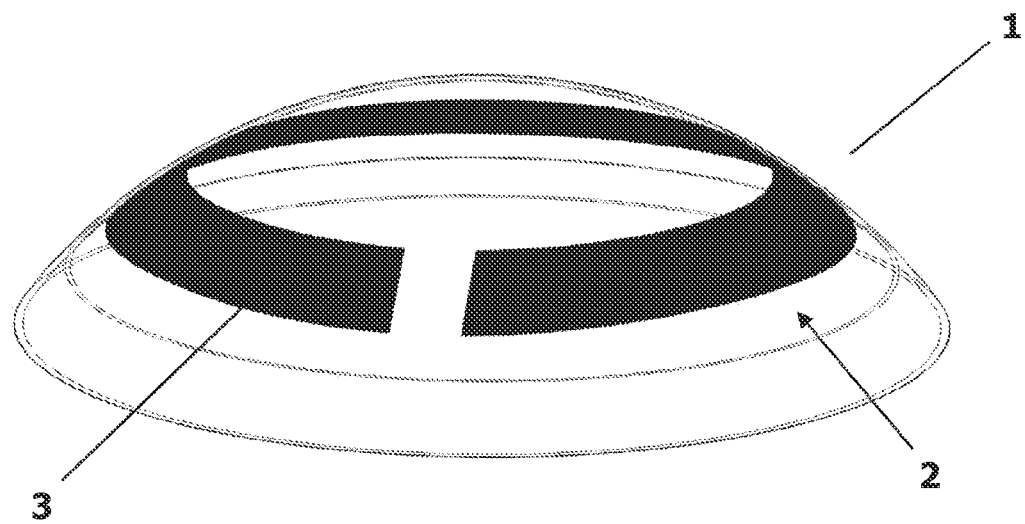
FIG. 1 demonstrates a top perspective view of an example of a contact lens with split-ring resonator (SRR) sensor embedded therein.
Figure 2:
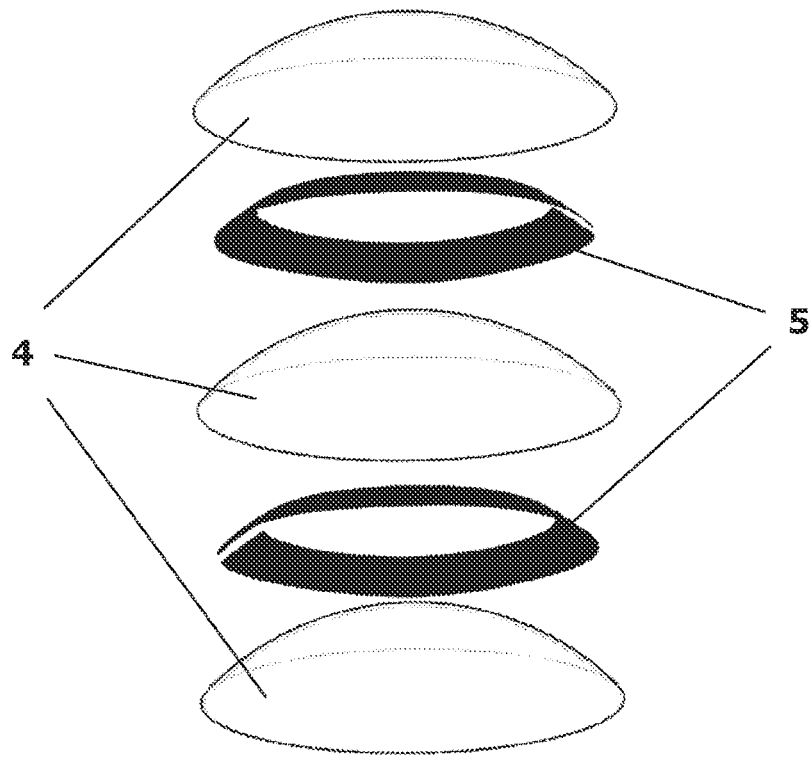
FIG. 2 demonstrates an exploded top perspective view of an example of a two-layer broadside-coupled split-ring resonator (BC-SRR) sensor.
Figure 3:
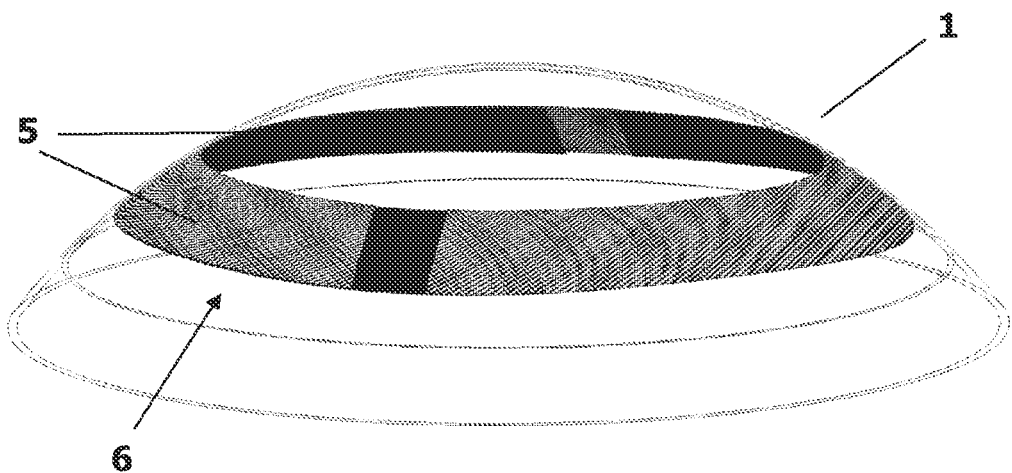
FIG. 3 demonstrates a top perspective view of an example of a broadside-coupled split-ring resonator (BC-SRR) sensor inserted within a contact lens.
Figure 4:
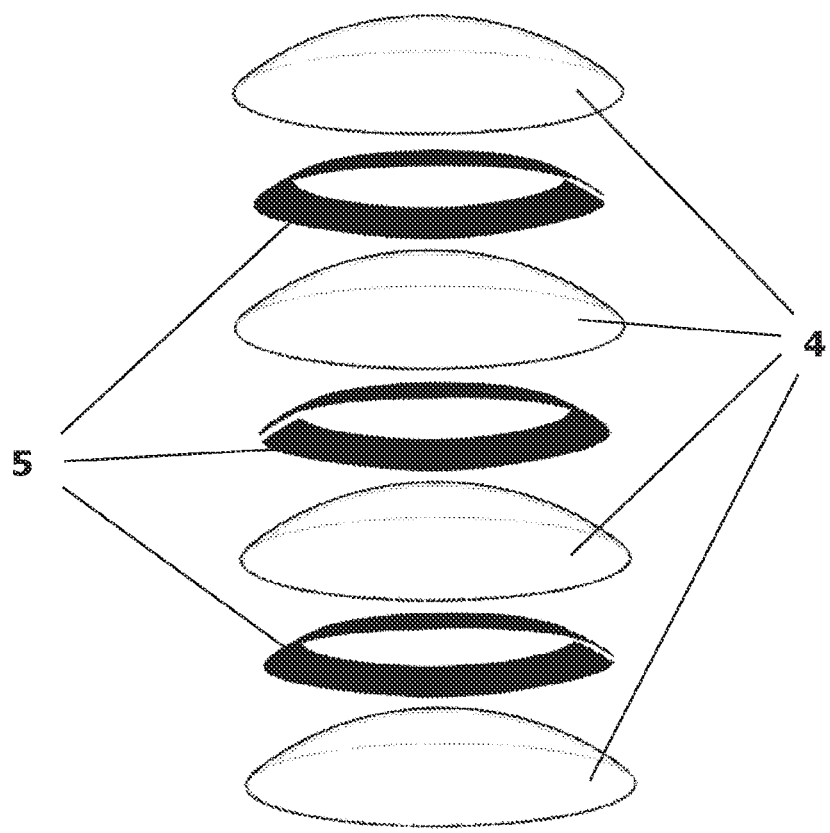
FIG. 4 demonstrates an exploded top perspective view of an example of a three-layer broadside-coupled split-ring resonator (BC-SRR) sensor.
Figure 5:
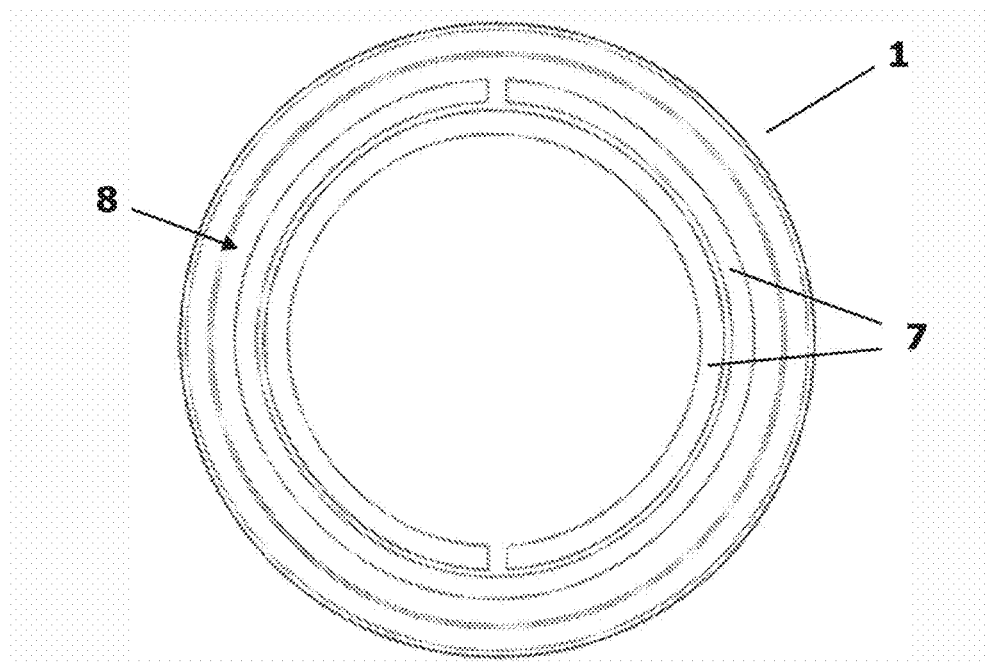
FIG. 5 demonstrates a top view of an example of a contact lens embedded with edge-coupled split-ring resonator (EC-SRR) sensor.
Figure 6:
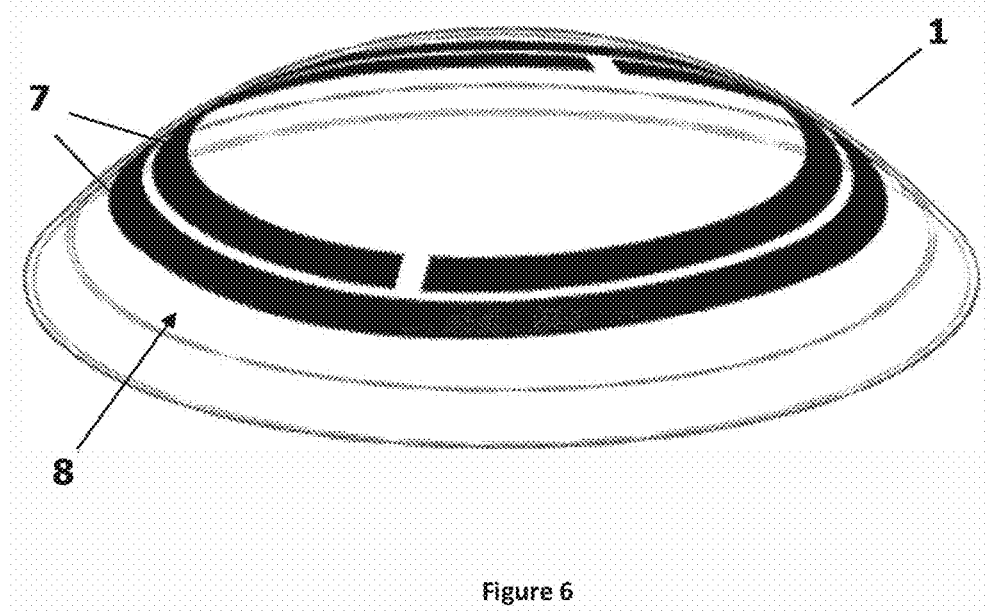
FIG. 6 demonstrates a top perspective view of an example of a contact lens embedded with edge-coupled split-ring resonator (EC-SRR) sensor.
Figure 7:
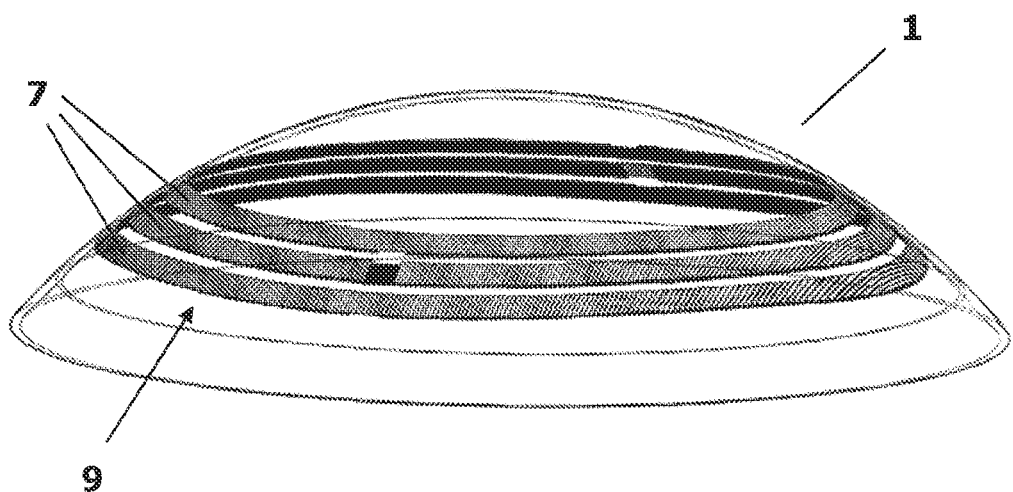
FIG. 7 demonstrates a top perspective view of an example of a contact lens embedded with two-layer, three-ring edge-coupled split-ring resonator (EC-SRR).
Figure 8:
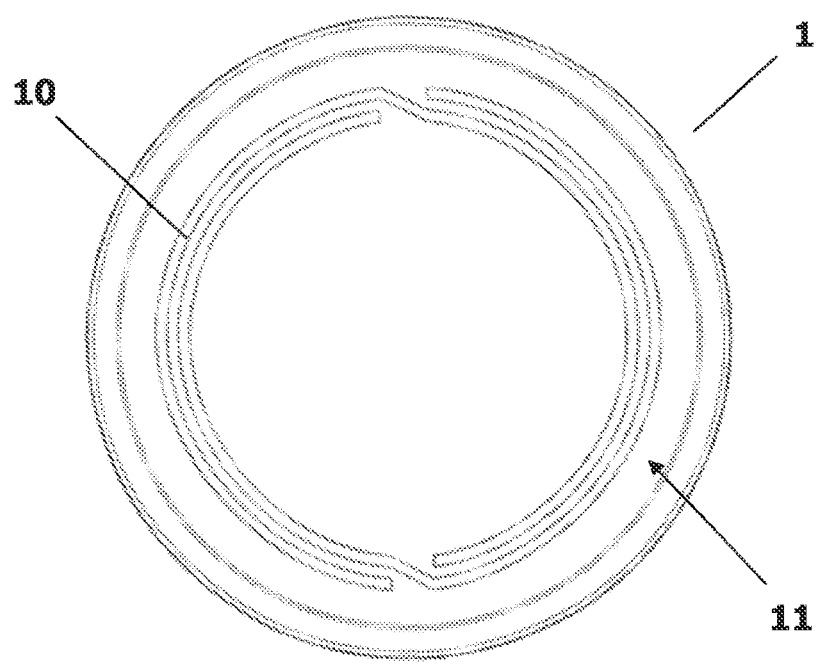
FIG. 8 demonstrates a top view of an example of a non-bianisotopic split-ring resonator (NB-SRR) sensor.
Figure 9:
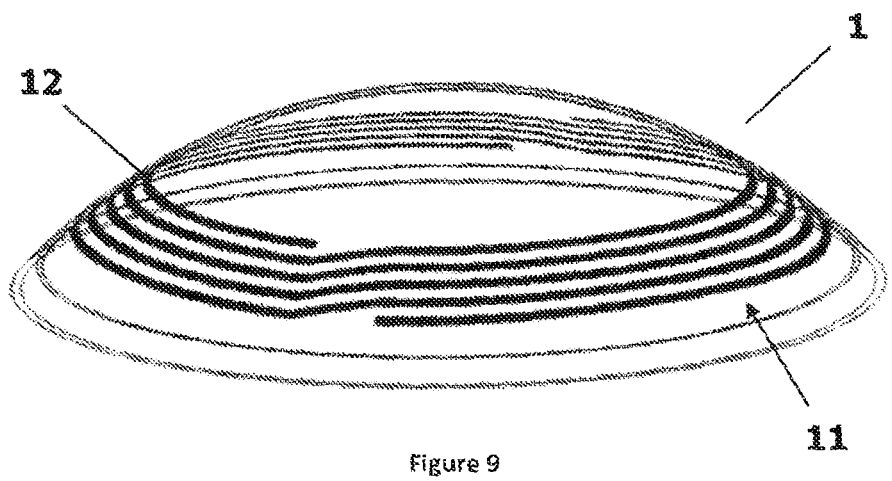
FIG. 9 demonstrates a top perspective view of an example of an alternative non-bianisotopic split-ring resonator (NB-SRR) sensor embedded within a contact lens.
Figure 10:
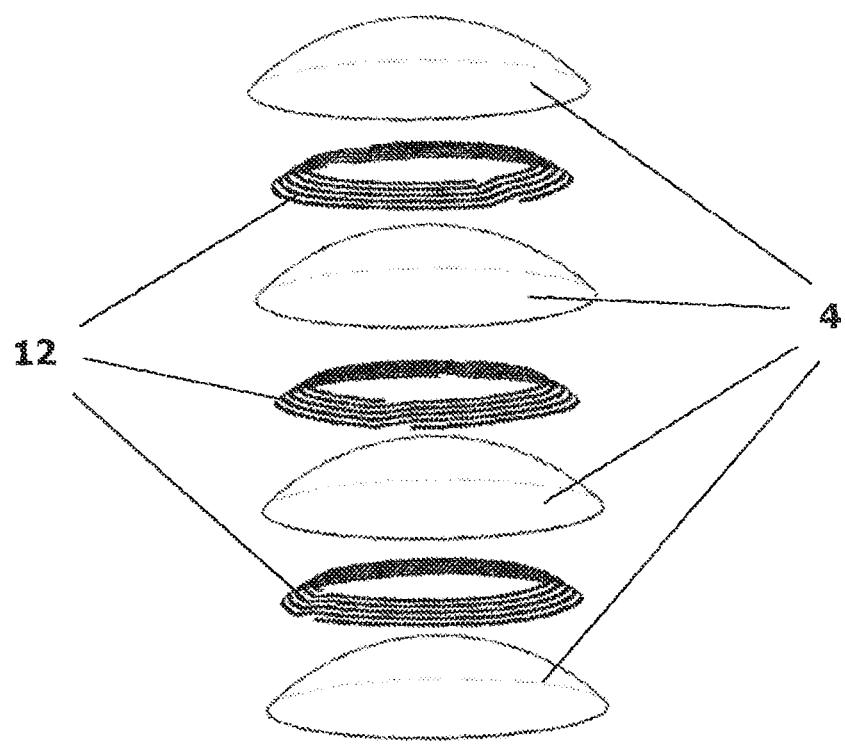
FIG. 10 demonstrates an exploded top perspective view of an example of a three-layer non-bianisotopic split-ring reasonator (NB-SSR) sensor.
Figure 11:
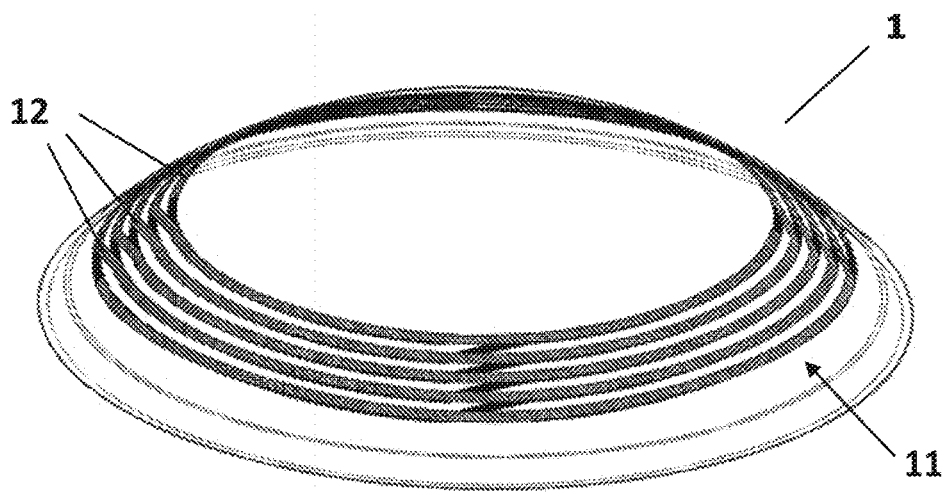
FIG. 11 demonstrates a top perspective view of an example of a two-layer non-bianisotopic split-ring resonator (NB-SRR) sensor embedded within a contact lens.
Figure 12:
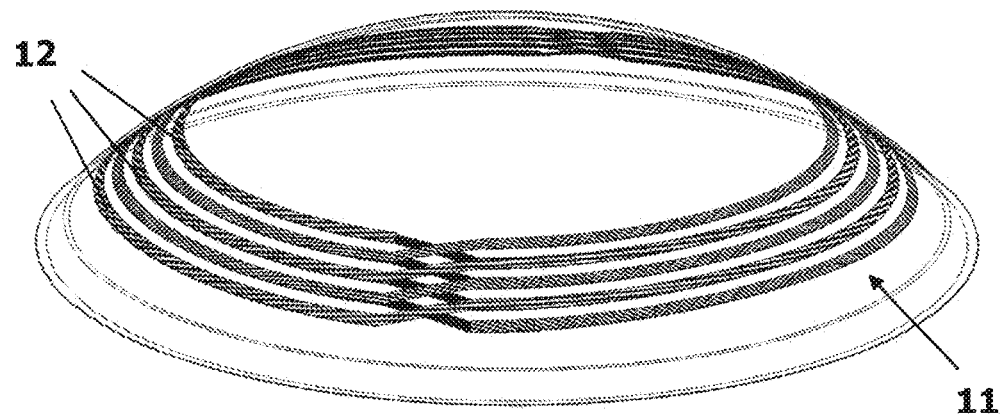
FIG. 12 demonstrates a top perspective view of an example of a NB-SRR sensor with half rings of different layers connected oppositely to be mirrors of each other.
Figure 13:
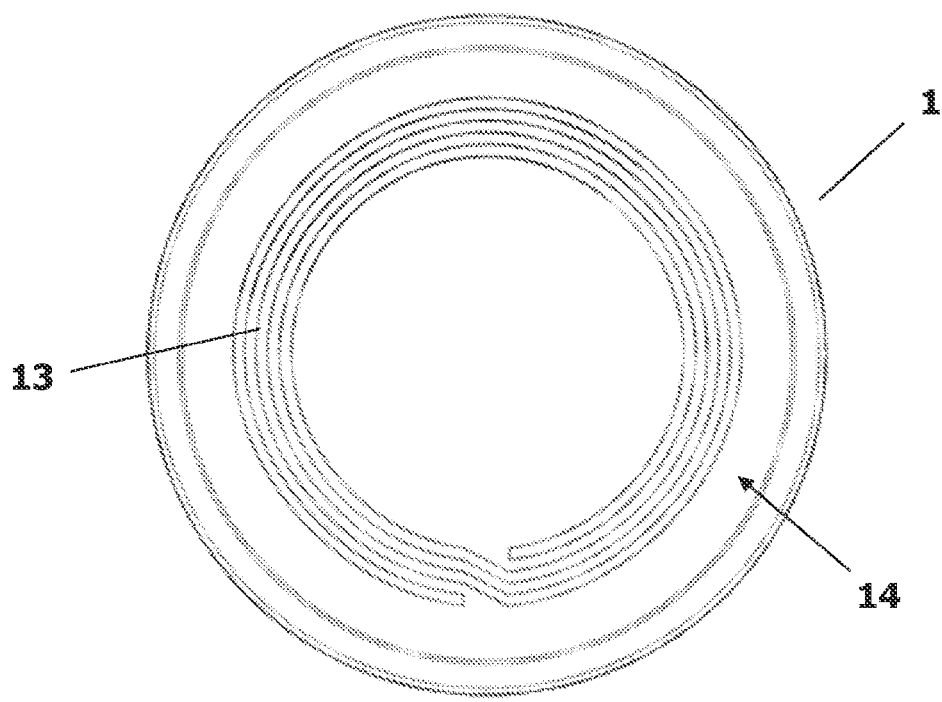
FIG. 13 demonstrates a top view of an example of a spiral resonator in a contact lens.
Figure 14:
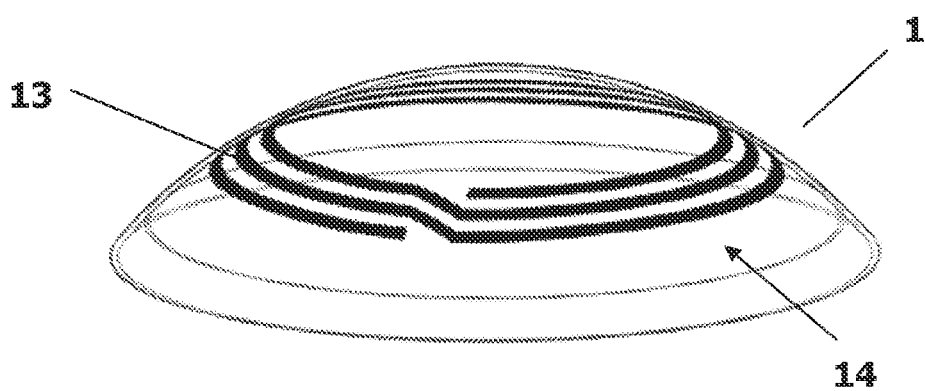
FIG. 14 demonstrates a top perspective view of an example of a spiral resonator in a contact lens.
Figure 15:
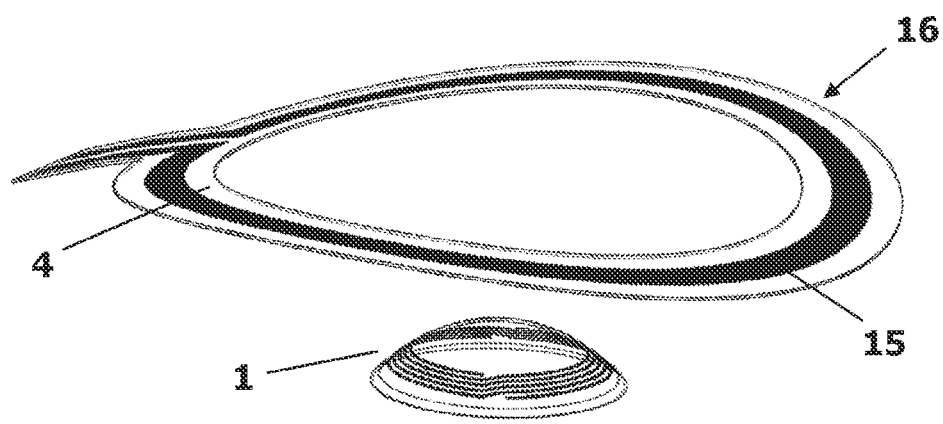
FIG. 15 demonstrates an example of a loop-type antenna on a flexible substrate positioned to collect measurements from a sensor-embedded contact lens.
Figure 16:
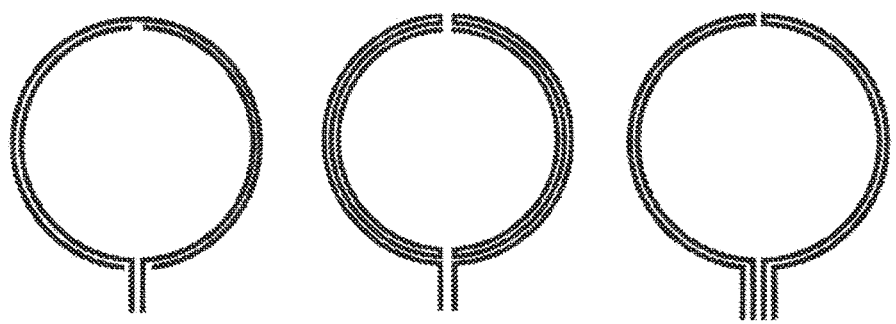
FIG. 16 demonstrates an example of alternative loop-type antennas for measurement collection.
Figure 17:
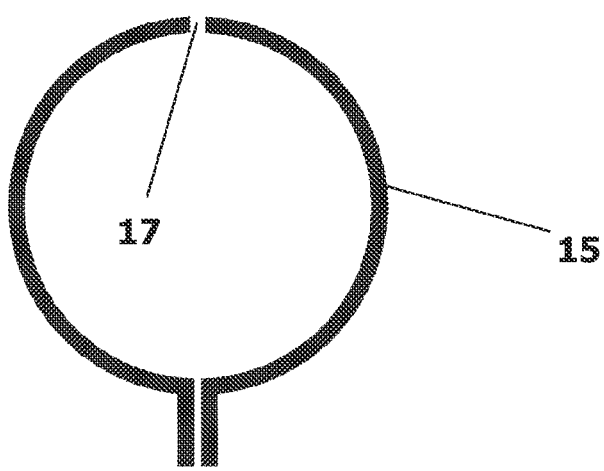
FIG. 17 demonstrates an example of an alternative loop-type antenna with a passive tuning element connected along its gap.
Figure 18:
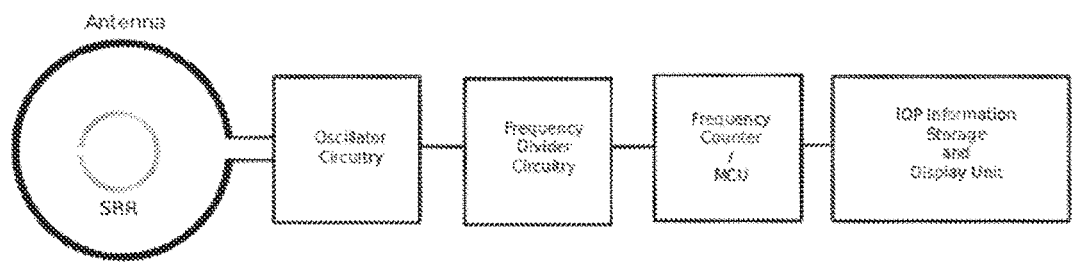
FIG. 18 demonstrates an example of an oscillator-based readout topology for a one port antenna configuration.
Figure 19:
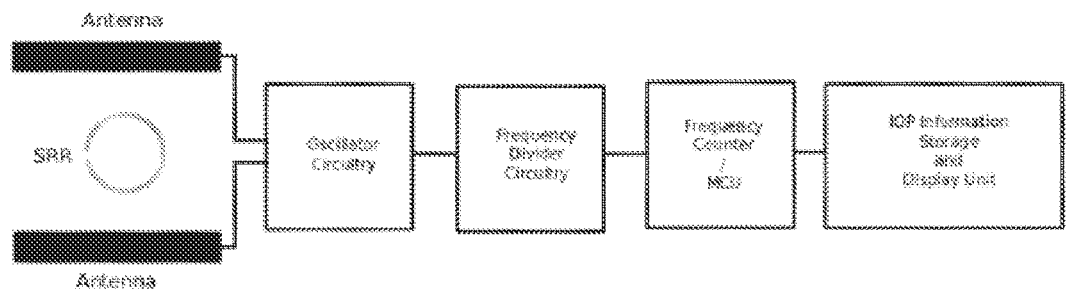
FIG. 19 demonstrates an example of a oscillator-based readout topology for a two port antenna configuration.
Figure 20:
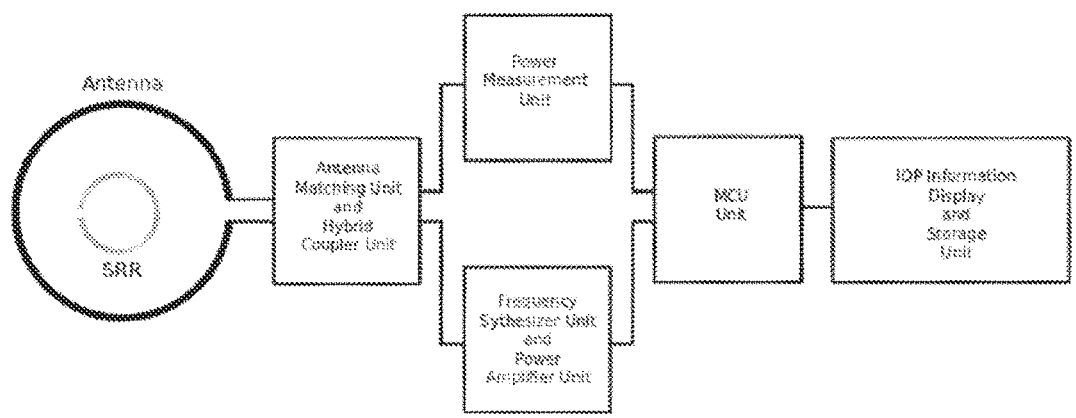
FIG. 20 demonstrates an example of a power spectrum-based readout topology for a one port antenna configuration.
Figure 21:
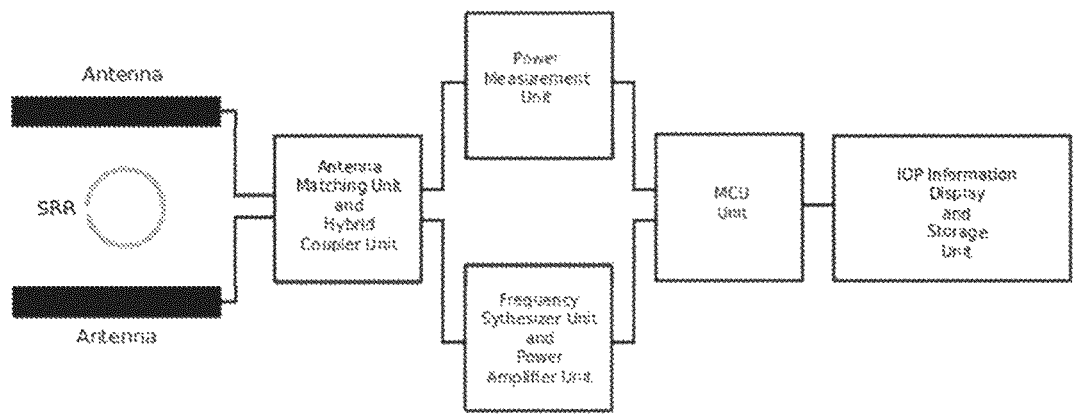
FIG. 21 demonstrates an example of a power spectrum-based readout topology for a two port antenna configuration.
Figure 22:
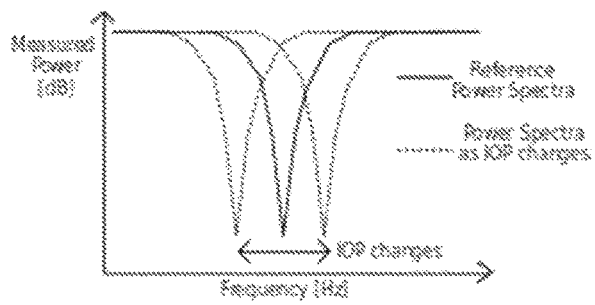
FIG. 22 demonstrates an example of a power spectrum performance graph.
Figure 23:
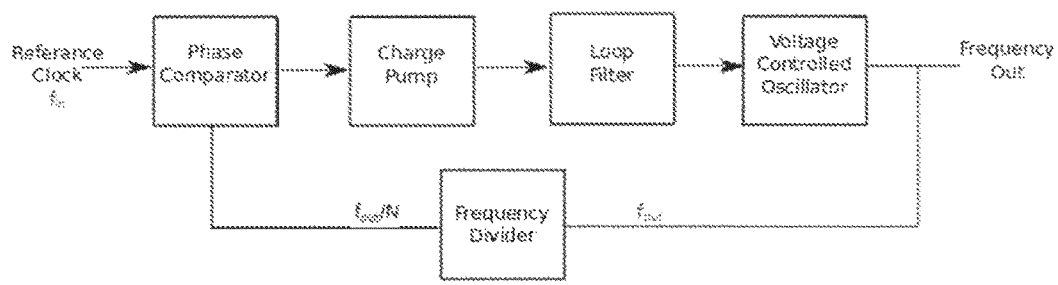
FIG. 23 demonstrates an example of a phase-locked loop (PLL) readout topology configuration.
Figure 24:
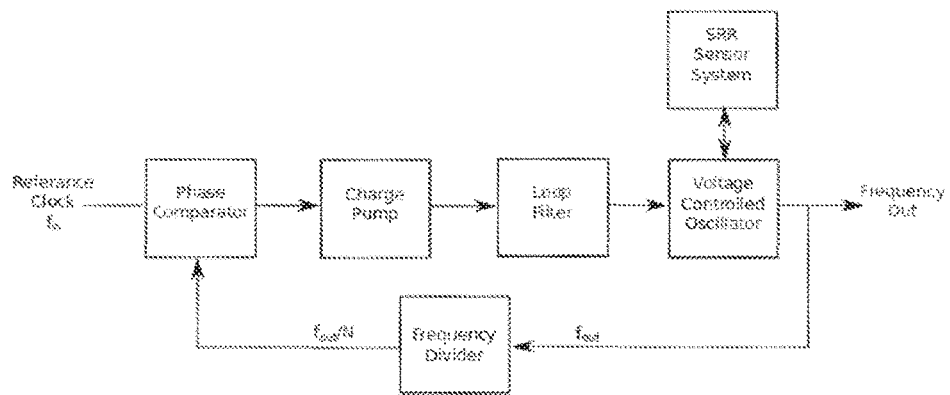
FIG. 24 demonstrates an example of a readout schema with a PLL in which the SRR sensor tunes the VCO.
Figure 25:
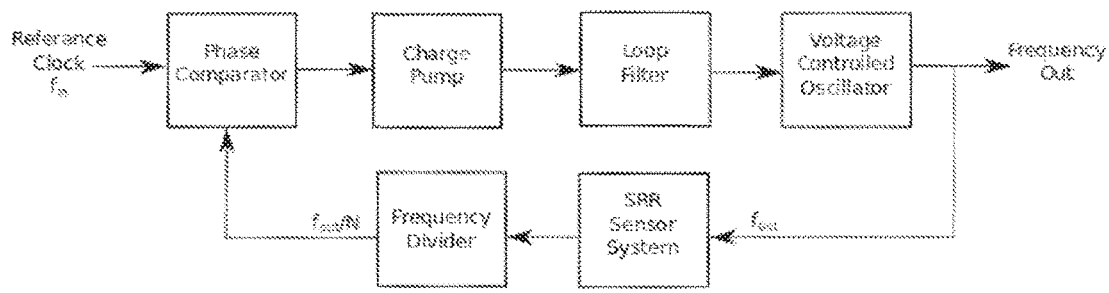
FIG. 25 demonstrates an example of a readout schema with a PLL in which the SRR sensor is implemented before the frequency divider.
Figure 26:
FIG. 26 demonstrates an example of an LC-equivalent circuit of a one-port, antenna coupled SRR structure.
Figure 27:
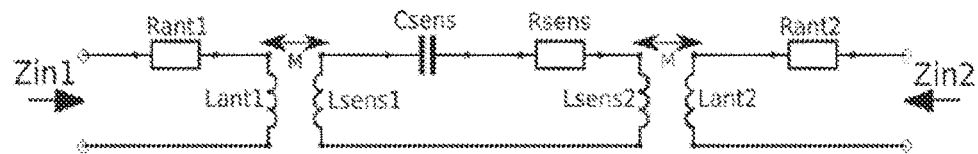
FIG. 27 demonstrates an example of a LC-equivalent of a two-port, antenna coupled SRR structure.
Figure 28:
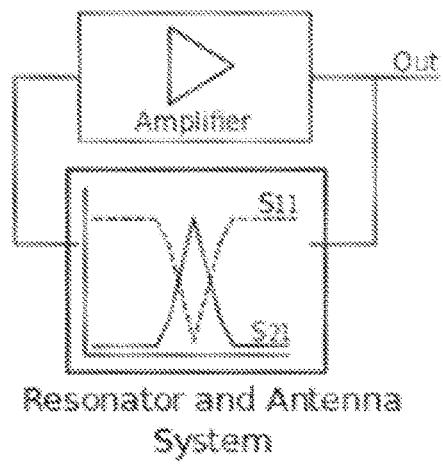
FIG. 28 demonstrates an example of a topology for a positive-feedback oscillator.
Figure 29:
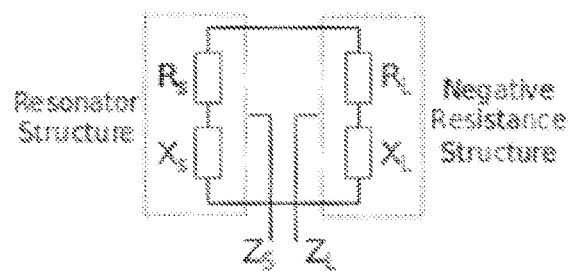
FIG. 29 demonstrates an example of a topology for a negative resistance oscillator.
Figure 30:
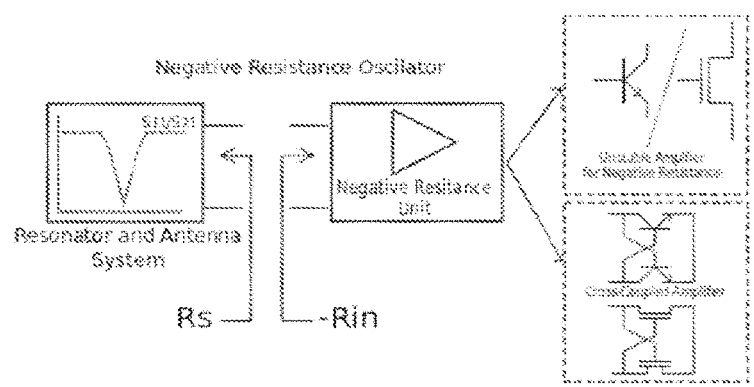
FIG. 30 demonstrates an example conceptualization of a negative resistance oscillator.

The following numerals are referred to in the detailed description:
1. Contact lens
2. Sensor
3. Resonator ring
4. Substrate layer
5. Broadside-coupled SRR
6. BC-SRR sensor
7. Edge-coupled SRR
8. EC-SRR sensor
9. Three-ring EC-SRR sensor
10. Non-bianisotropic SRR
11. NB-SRR sensor
12. Alternative NB-SRR
13. Spiral resonator
14. Spiral resonator sensor
15. Antenna loop
16. Antenna
17. Passive tuning element Disclosed is a contact lens embedded sensor system for accurate detection and monitoring of a group of ocular disorders associated with a common diagnostic feature marked by high intraocular pressure (IOP) associated optic neuropathy, namely glaucoma. High IOP is an etiological factor of ocular hypertension, which is the most common precursor of open-angle glaucoma. The aqueous humour produced by the ciliary body of the eye may be the main culprit of intraocular pressure. If the drainage through the trabecular meshwork is slower than the aqueous humour production, IOP starts to increase. Increase of IOP results in ocular hypertension may lead to optic nerve damage and permanent vision loss (glaucoma) for some people. As a precursor of ocular hypertension and glaucoma, IOP should be observed with regular, timely measurements.

As summarized earlier, a non-invasive continuous, IOP monitoring sensor system may include differing instances of metallic resonator design structures on a biocompatible, flexible substrate; antennas in the proximity of said metallic resonator for obtaining measurements, and an electronic readout circuitry for processing said measurements and data obtained. Metallic resonator rests situated within a contact lens preferably on top of the corneoscleral limbus where frequency shift change is the maximum, may be positioned to follow and detect the presence of corneal deformation induced by an increase in IOP. The system is capable of measuring the changes in the resonant frequency of the resonator, depending on the curvature/circumferential variation of the substrate to monitor changes in IOP.

Wearable contact lens (1) with embedded sensor (2) is configured as a passive element, conforms on the eye as its design counterparts; forming a secondary physical relationship between the eye and sensor (2) contained therein. Contact lens (1) is preferably manufactured from a poly (dimethylsiloxane) dialkanol (PDMS)-hydrogel material which enables complicity with dielectric nature of the sensors (2). Sensors (2) comprise resonator rings (3), which themselves possess different design specifications as mutually inclusive alternatives, mainly concerning the topology of any one or more of split ring resonators (5, 7, 10). One embodiment includes a resonator ring (3) which, is a plain split-ring resonator (5, 7, 10) based structure, that consequently can be modelled as an equivalent parallel LC circuit. The self-inductance of the resonator ring (3) may be the equivalent inductance, while its gap capacitance, surface capacitance and capacitance between more than one resonator rings (3) may form the equivalent capacitance. The nominal resonant frequency of the LC circuit may be optimized by changing the number, thickness(es) of the dielectric substrate(s) and the dimensions of the resonator rings (3). Fluctuations in IOP often result in deformation of the eyeball that translates to changes in geometry on a contact lens (1) sitting conformally on the eyeball.

Pertaining to the nominal resonant frequency optimization described above, a contact lens (1) with broadside-coupled split-ring resonator (BC-SRR) (5) sensor (2) may include two rings of angular orientations of 180° with flexible, transparent, dielectric biocompatible substrate layers (4) between them, which, along with physically separating different rings, may enable insulation between surrounding surfaces and render the use of the sensor within a contact lens (1). Broadside-coupled SRR sensor (6) may or may not include additional transparent, dielectric, flexible, biocompatible substrate layers (4) on top and bottom of the broadside-coupled SRR (5) elements for further covering according to different embodiments. In a broadside-coupled SRR (5), the gaps on each resonator ring (3) serve the purpose of causing the electric current to flow from one split-ring to another; as a displacement current through the biocompatible substrate layer (4). Therefore, the gap between the resonator rings (3), the gaps on each resonator ring (3), and the surface capacitances of the split-rings can be modelled as capacitances and its inductance can be defined as the self-inductance of the split-rings, which form an equivalent parallel LC circuit when considered together in the form of a lens (1) with broadside-coupled SRR sensor (6).

Broadside-coupled SRR sensors (6) may also alternatively contain three resonator rings (3) having 120° angular orientation, with the addition of one biocompatible substrate layer (4) at either occasion to bring about the three-ring containing broadside-coupled SRR (5). Dimensions and geometries of said two or three rings bringing together the broadside-coupled SRR (5) may be similar or different according to separate embodiments.

Another split-ring resonator design includes edge coupling, producing sensors (2) with edge-coupled split-ring resonator (EC-SRR) (7): An edge coupled SRR (7) consists of two concentric metallic rings with different radii, their gaps facing opposite directions, standing on or embedded in a flexible, transparent, biocompatible dielectric substrate layer (4). More than two concentric rings can also be used; however according to a preferred embodiment edge-coupled SRR (7) has a single layer. A multi-layered edge-coupled SRR (7) structure may also be realized according to another embodiment. Different layers may or may not be rotated 90 or 180 degrees with a flexible, transparent, biocompatible dielectric substrate (4) in between, in yet another embodiment of a three-ring EC-SRR sensor (9). The dimensions and the geometries of the split-rings can be similar to or different from each other according to different embodiments.

Another split-ring resonator design includes non-bianisotropic approach, producing a contact lens (1) with sensors (2) comprising non-bianisotropic split-ring resonator (NB-SRR) (10): A non-bianisotropic SRR (10) consists of two half rings of a circular ring connected to two opposite half rings of an outer concentric circle on the same plane. More than two rings can also be used to expand the structures. The structure can be standing on or embedded in a flexible, transparent, dielectric biocompatible substrate layer (4). A multi-layered, alternative non-bianisotropic SRR (12) structure may also be realized according to another preferred embodiment. Different layers may or may not be rotated 90 degrees with a flexible, transparent, biocompatible dielectric substrate (4) in between. NB SRR's of different layers may have their half rings connected oppositely, such that they are mirrors of each other. The dimensions and the geometries of split-rings can be similar to or different from each other according to different embodiments.

Next to aforementioned designs centered around split-ring resonators (5, 7, 10), a spiral resonator (13) may also be used as a sensor to realize a spiral resonator sensor (14), so that a lower resonance frequency may rendered possible using similar dimensions. The spiral structure can be monofilar or multifilar, which changes its resonant behaviour. Spiral resonator (13) may be standing on or embedded in a flexible, transparent, dielectric biocompatible substrate layer (4). Still alternatively, a multi layered monofilar or multifilar resonator structure can be realized as the sensor(s) (2), with flexible, transparent, dielectric biocompatible substrate layer (s) (4) in between. The spiral resonators (13) at different layers may or may not be rotated 90 degrees. Spirals of different layers may have their rings connected oppositely, such that they are mirrors of each other. The dimensions and the geometries of spirals can be similar to or different from each other according to different embodiments.

Alternatively, one sensor (2) may contain more than one types/instances of resonator types in the same substrate, where each said resonator can be SRR-based (5, 7, 10), or monopoles realized as strips of conductor, or any other resonator structure. When measuring such a sensor with more than one resonator, the frequency response may be inspected such that the resonance caused by one or more structures may be taken as reference value for calibration purposes.

Dimensions of the conductive materials which define resonator rings (3), and in turn split-ring resonators (5, 7, 10) of any design spec are arranged such that the inner radius of the conductive layer is made larger than the maximum pupil radius in the dark, which is 8 mm in diameter, in order to maintain normal field of view (FOV) of the patient. The split-rings that form the split-ring resonators (5, 7, 10) are made of biocompatible metals such as gold, titanium and chromium. Split-ring resonators (5, 7, 10) can be circular or polygonal in shape.

In a preferred embodiment, flexible dielectric biocompatible substrate layer (4) is made of biocompatible transparent polymers with low swelling rate such as PDMS, PI, Poly (methyl methacrylate) (PMMA), Parylene, Silicone or polyethylene terephthalate (PET) to avoid beclouding or obscuring the patient's vision and to minimize dielectric constant variations arising from potential water absorption. Alternatively, if non-transparent biocompatible material is used, the flexible dielectric biocompatible substrate layer (4) can be realized with a central hollow which is wider than 8 mm in diameter, not compromising the function and integrity of any sensor (2) or SSR or spiral resonators (5, 7, 9, 10, 12) with the light rays having zero contact with said biocompatible substrate layer (4) and thus only optic relationship established is merely between the contact lens (1) and pupil of the patient.

The thickness of both SRR's and spiral resonators (5, 7, 9, 10, 12) can be varied between 50 nm to 20 μm, depending on the electrical and mechanical properties of the conductive layer. The thickness of the dielectric substrate layer(s) (4) can be varied from 1 μm to 100 μm. The width of the conductive layer can be varied from 0.05 mm to 2.5 mm, which can be arranged so as to not disturb patient's vision. The widths and thicknesses of the metallic and dielectric layer can be optimised to tune nominal resonant frequency and quality factor (Q factor) of the resonator.

The resonators with flexible substrate layer (4) can be fabricated using various methods; such as in one specific method, the metallic layer of the sensors (2) are fabricated on carrier planar substrates such as silicon or glass wafer and the final shape of the sensor can be given while embedding in soft contact lens. The metallic shape of the resonator can be defined using photolithography. In another method, the metallic shape can be defined by mechanical or laser cutting processes using thin conductive sheets, metallised polymer substrates or wired laminates. In another method, the metallic shape can be defined using screen printing process by the help of stencils.

Disclosed sensor (2) does not require any electrical connection for operating, as it is purely passive. The resonant frequency of an SRR (5, 7, 10) may be wirelessly obtained from reflection or transmission characteristics by a receiving antenna (16), or a transmitting and receiving antenna pair. An antenna loop (15) is utilized to measure parameters to characterize the resonator according to one embodiment. Alternatively, a monopole antenna pair may be used to obtain transmission and reflection parameters. According to one embodiment, an antenna (16) comprising an antenna loop (15) situated in proximity with aptly shaped substrate layer (4) and a sensor (2), be it SRR (5, 7, 10) or spiral resonator sensor (14), construct a near field coupled system whose resonant frequency is determined by the resonator due to high-quality factor thereof. The multiplicity formed by sensor (2) and antenna (16) elements does not need any additional antenna (16), ground plane or active circuit elements placed in the contact lens (1).

Alternatively, other variants of a loop-antenna can be used. These loop-type antennas may have extra rings, each electrically connected or parasitically coupled to the driven ring. Antennas (16) may also feature gap(s), and a passive tuning element (17) can be connected across the gap(s), which enables control of the structures' frequency response.

In a preferred embodiment, the antenna(s) (16) can be mounted on a transparent patch able to be strapped on the patients' head across the eye and above the contact lens (1), to measure the frequency shifts of the resonator ring (3) embedded sensor (2) in the contact lens (1) worn by the patient. Alternatively, the antenna (16) may be mounted on eyeglasses, which would enable further proximity for obtaining measurements. Said antenna (15) may be comfortably worn by the patient in both cases such that the resonant dip can be tracked to indirectly measure the changes in intraocular pressure (IOP).

The unique structure of the sensor (2) may enable usage of different read-out circuitry approaches for measuring intraocular pressure (IOP). The resonance characteristic of the resonator (3) of the sensor (2) can be measured with an external antenna (15) coupled to the SRR (6, 8, 11) sensor (2). The transmitted or reflected power characteristics of the antenna (15) are affected by the SRR sensor (2). Because a high quality factor of SRRs' (6, 8, 11), the measured antenna characteristics are consequently determined by the sensor (2).

The sensing system can be integrated in an oscillatory circuit for different antenna configurations and the oscillator-based readout circuit can be utilized for resonance frequency measurement. A similar setup for one port or two port antennas can be used for this purpose. The readout circuitry consists of an oscillator circuitry with SRR sensor, a frequency divider and a processor circuitry, such as a micro-controller unit (MCU) for frequency counting. The processor circuitry may include a processor, memory, communication interface(s) and programmable input/output peripherals (I/O). The resonant frequency of the antenna coupled SRR sensor determines the oscillation frequency of the oscillator circuitry. The change in IOP shifts the resonant frequency of the sensor and it causes a shift in the frequency of the oscillator output signal. The output signal frequency of the oscillator is divided or down-converted by a frequency divider or a mixer, which makes it possible to measure output frequency by a frequency counter or a micro controller unit. The micro-controller transmits, or stores measured IOP information. The change between the resonance frequency versus IOP can be measured by the scheme described above.

The oscillator-based circuitry can be realized with a single antenna or a pair of antennas in a transmit/receive configuration. Negative resistance or positive feedback oscillator circuitry topologies may be used in the readout circuitry. The positive feedback-based oscillator circuitry is more suitable for antenna pairs, while negative resistance-based oscillators circuitry can be used with both configurations.

Alternatively, a measurement methodology based on power spectrum can be used for resonant frequency measurement. Readout circuit based on power measurement technique may include a processor circuitry such as an MCU, a frequency synthesizer, a power detector, and an antenna matching circuit with/without hybrid couplers. The processor circuitry, such as an MCU, may control the frequency synthesizer and scans a frequency range in which the sensor resonates. For each frequency scan instance, power measurement is taken by the power detector and the measured power information may be digitized by the processor circuitry, such as an MCU. The antenna matching and hybrid coupler units are configured to measure reflected or transmitted power. The changes in resonant frequency may be tracked with the power-frequency spectrum data given by the readout circuitry. For different antenna configurations, the transmitted power through sensor or reflected power from the sensor can be measured, which makes it possible to use a single antenna or an antenna pair configuration like loop-type or a pair of monopole/dipole antennas. The change in resonant frequency or the power at the resonant frequency is then interpreted as IOP information. This topology allows using any antenna configuration for measuring resonance of the sensor (2) and benefits from not only frequency change but also power change at certain resonant frequencies.

A phase-locked loop (PLL) system is another alternative for a readout circuitry, which has improved phase noise characteristics and accuracy. The typical PLL structure consists of a reference clock, a phase comparator, a charge pump, a loop filter (low-pass filter), a voltage-controlled oscillator (VCO) and a frequency divider unit. It works in the basis of making the output frequency a given fraction of the reference clock. Therefore, in a PLL system, the output frequency synthesized by the VCO unit is divided by the frequency divider. Then, the output of the frequency divider is compared to the reference clock by the phase comparator. Afterwards, a charge pump is used to generate the charge for capacitors in the loop filter. The loop filter integrates error to generate VCO tuning voltage. With this schema, the output frequency is progressively compared with reference clock and the VCO is tuned until the divided output frequency equals the reference clock.

The readout circuitry by using a PLL unit can be realized with different configurations for the disclosed system, such is an alternative PLL-based option for readout-circuitry. According to one embodiment, the SRR sensor is integrated into the VCO unit of the PLL system. The VCO in this technique can be realized by any oscillator architecture mentioned earlier by a small modification using varactor diodes. IOP variations change the resonant frequency of the resonator. The change of resonance frequency creates a difference between the output of the frequency divider and the reference clock. This difference is used as a tuning voltage at the output of the loop filter and changes the capacitance of the varactor in the VCO. The tuning will continue until the phases of the reference clock and the signal at output of the frequency divider are locked. The frequency change can be read from the value of the frequency divider or the output voltage of the loop filter. This methodology creates a fast and accurate measurement option, with a high Q factor that causes low phase noise levels. With this architecture, the speed and accuracy can be greatly increased.

Another alternative is using the split-ring resonator sensor system in front of the frequency divider, in which configuration, an SRR sensor system whose transmission characteristics demonstrate a peak at certain frequency is needed. The loop stabilizes at only a certain frequency, increasing the phase noise immunity. An SRR which has a band-stop characteristic can also possibly be used. Similarly, the frequency change can be related to the output value of the frequency divider or the output voltage of the loop filter.

Alternatively, the split-ring resonator based sensor system may be used before/instead of the loop filter. This architecture, marked with a great Q factor incidentally becomes ideal for a filter application, consequently making very low phase noise levels possible. The readout of the frequency change can be made with similar methods to the other PLL readout circuitries defined herein.

In a nutshell, the system includes a contact lens (1) with a sensor (2) comprising resonator rings (3) embedded therein, separated by flexible, dielectric, biocompatible insulation layers (4) for continuous measuring of intraocular pressure, as readout circuitry topologies enable conversion of physical quantity of changing eye geometry in order for its interpretation as increase/decreases in intraocular pressure.

In one aspect of the disclosed system, a contact lens embedded sensor system for IOP monitoring in ocular hypertension and glaucoma conditions, comprising at least one contact lens (1) with one sensor (2) embedded therein along with at least one antenna (16) coupled to said at least one contact lens (1) and electronic readout circuitry is proposed.

In one aspect of the disclosed system, said sensor (2) comprises split-ring resonator type and/or low-resonant frequency spiral resonator (13) type resonator rings (3) with identical resonance characteristics and at least one flexible biocompatible substrate layer (4) in between.

In one aspect of the disclosed system, a contact lens embedded sensor system for glaucoma monitoring, comprising at least one contact lens (1) with one sensor (2) embedded therein along with at least one antenna (16) coupled to said at least one contact lens (1) and electronic readout circuitry is proposed.

In one aspect of the disclosed system, said sensor (2) comprises at least two split-ring resonator type resonator rings (3) with identical resonance characteristics and at least one flexible biocompatible substrate layer (4) in between.

In another aspect of the disclosed system, said contact lens embedded sensor system is a passive structure continuously configured to sense intraocular pressure (IOP).

In another aspect of the disclosed system, said sensor (2) comprises at least two low-resonant frequency spiral resonator (13) type resonator rings (3) with and at least one flexible biocompatible substrate layer (4) in between.

In another aspect of the disclosed system, said contact lens embedded sensor system is a passive structure continuously configured to sense intraocular pressure (IOP).

In another aspect of the disclosed system, said one sensor (2) is a broadside-coupled split ring resonator sensor (6) comprising broadside-coupled split-ring resonator(s) (5).

In another aspect of the disclosed system, said one sensor (2) is an edge-coupled split ring resonator sensor (8) comprising edge-coupled split-ring resonator(s) (7).

In another aspect of the disclosed system, said one sensor (2) is a non-bianisotropic split ring resonator sensor (11) comprising non-bianisotropic split-ring resonator(s) (10).

In another aspect of the disclosed system, said sensor read-out circuitry comprises a positive-feedback oscillator architecture.

In another aspect of the disclosed system, said sensor read-out circuitry comprises a negative-resistance oscillator circuitry architecture.

In another aspect of the disclosed system, said sensor (2) comprises at least one substrate layer (4) manufactured from a material selected from a group including PDMS, PI, PMMA, Parylene, Silicone or PET to avoid clouding.

In another aspect of the disclosed system, said antenna (16) coupled to said sensor (2) comprised by said contact lens (1) over an apparatus in the form of eyeglasses.

In another aspect of the disclosed system, said antenna (16) coupled to said sensor (2) comprised by said contact lens (1) over an apparatus in the form of a patch headgear.

In another aspect of the disclosed system, said readout electrical circuitry comprises an oscillator circuitry coupled to the antenna, a frequency divider circuitry, and a frequency counter or processor circuitry, such as a microcontroller unit (MCU).

In another aspect of the disclosed system, said readout electrical circuitry comprises an antenna matching hybrid coupler, a power measurement unit and frequency synthesizer/power amp in parallel, and processor circuitry, such as a microcontroller unit (MCU).

In another aspect of the disclosed system, said readout electrical circuitry comprises a phase comparator, a charge pump, a loop filter, a voltage controlled oscillator (VCO) and a frequency divider.

In another aspect of the disclosed system, said readout electrical circuitry further comprises an SRR sensor system coupled to the voltage controlled oscillator (VCO).

In another aspect of the disclosed system, said readout electrical circuitry further comprises an SRR sensor system between said voltage controlled oscillator (VCO) and said frequency divider.

According to one aspect of the disclosed system, a method of monitoring intraocular pressure (IOP) operating a contact lens embedded sensor system is proposed.

In another aspect of the disclosed system, said method comprises a step of resonant frequency shift, where a contact lens (1) comprising sensor (2) with resonator rings (3) undergoes change in geometry caused by increased intraocular pressure (IOP).

In another aspect of the disclosed system, said method comprises a step of shift perception, where the antenna (16) configuration coupled to said resonator element comprising an antenna loop (15) on a substrate layer (4) detecting said resonant frequency shift.

In another aspect of the disclosed system, said method comprises a step of processing, where said resonant frequency shift measurements are collected and processed by an electronic readout circuitry and interpreted as a change in intraocular pressure (IOP).

In another aspect of the disclosed system, said method comprises a step of said electronic readout circuitry processing comprises different topologies for one port and two port antenna (16) configurations.

In another aspect of the disclosed system, said method comprises a step of signal generation, where the resonant frequency of antenna (16) coupled SRR sensor determines the oscillation frequency of the oscillator circuitry and delivers an oscillator output signal.

In another aspect of the disclosed system, said method comprises a step of division/downconversion, where said oscillator output signal is divided or downconverted by a frequency divider or a mixer.

In another aspect of the disclosed system, said method comprises a step of measurement, where a frequency counter or processor circuitry, such as an MCU, measures the output frequency for resonance frequency vs. intraocular pressure (IOP) change.

In another aspect of the disclosed system, said method comprises a step of measurement, where the antenna matching and hybrid coupler units measuring reflected or transmitted power.

In another aspect of the disclosed system, said method comprises a step of scan, where processor circuitry, such as the MCU-controlled frequency synthesizer scans a frequency range in which the sensor resonates.

In another aspect of the disclosed system, said method comprises a step of measurement, where the power detector collects power measurements for each scanned frequency.

In another aspect of the disclosed system, said method comprises a step of digitization, where the measured power information is digitized by processor circuitry, such as the MCU.

In another aspect of the disclosed system, said method comprises a step of synthesis, where an output frequency is synthesized by a voltage controlled oscillator (VCO) unit.

In another aspect of the disclosed system, said method comprises a step of frequency division, where said output frequency is divided by a frequency divider.

In another aspect of the disclosed system, said method comprises a step of comparation, where the output of said frequency divider is compared to the reference clock by the phase comparator.

In another aspect of the disclosed system, said method comprises a step of generation, where a charge pump generates the charge for capacitors in the loop filter.

In another aspect of the disclosed system, said method comprises a step of tuning, where the loop filter integrates error to generate VCO tuning voltage.

In another aspect of the disclosed system, said electronic readout circuitry based processing further comprises a recursive execution of said steps until the divided output frequency equals the reference clock.

The methods, devices, processing, circuitry, and logic described above may be implemented in many different ways and in many different combinations of hardware and software. For example, all or parts of the processing circuitry may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die.

Accordingly, the circuitry may store or access instructions for execution, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or other storage circuitry; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways.

In some examples, each unit, subunit, and/or module of the system, such as the processor unit may include one or more logical components. Each logical component may be hardware or a combination of hardware and software. For example, each logical component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each logical component may include memory hardware, such as a portion of the memory, for example, that comprises instructions executable with the processor or other processors to implement one or more of the features of the logical components. When any one of the logical components includes the portion of the memory that comprises instructions executable with the processor, the logical component may or may not include the processor. In some examples, each logical components may just be the portion of the memory or other physical memory that comprises instructions executable with the processor or other processor to implement the features of the corresponding logical component without the logical component including any other hardware. Because each logical component includes at least some hardware even when the included hardware comprises software, each logical component may be interchangeably referred to as a hardware logical component.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . or <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

While various embodiments have been described, it will be apparent to those of ordinary skill in the art that many more embodiments and implementations are possible. Accordingly, the embodiments described herein are examples, not the only possible embodiments and implementations.

The invention claimed is:

1. A contact lens embedded sensor system for intraocular pressure (IOP) monitoring in ocular hypertension and glaucoma conditions, comprising: a contact lens with a sensor embedded therein, an antenna coupled to said sensor, and an electronic readout circuitry, wherein said sensor comprises at least two resonator type resonator rings, the at least two resonator type resonator rings stacked on top of each other with at least one flexible biocompatible substrate layer sandwiched in between, wherein said contact lens embedded sensor system is a passive structure continuously configured to sense intraocular pressure (IOP), and wherein said electronic readout circuitry comprises an antenna matching hybrid coupler, a power measurement unit and a frequency synthesizer/power amp in parallel, and a microcontroller unit (MCU).

2. The contact lens embedded sensor system for IOP monitoring in ocular hypertension and glaucoma conditions as set forth in claim 1, wherein the at least two resonator type resonator rings are at least two split ring resonator type resonator rings with identical resonance characteristics.

3. The contact lens embedded sensor system for IOP monitoring in ocular hypertension and glaucoma conditions as set forth in claim 2, wherein said sensor is a broadside-coupled split ring resonator sensor comprising a broadside-coupled split-ring resonator.

4. The contact lens embedded sensor system for IOP monitoring in ocular hypertension and glaucoma conditions as set forth in claim 2, wherein said sensor is an edge-coupled split ring resonator sensor comprising an edge-coupled split-ring resonator.

5. The contact lens embedded sensor system for IOP monitoring in ocular hypertension and glaucoma conditions as set forth in claim 2, wherein said sensor is a non-bianisotropic split ring resonator sensor comprising a non-bianisotropic split-ring resonator.

6. The contact lens embedded sensor system for IOP monitoring in ocular hypertension and glaucoma conditions as set forth in claim 1, wherein the at least two resonator type resonator rings are at least two spiral resonator type resonator rings.

7. The contact lens embedded sensor system for IOP monitoring in ocular hypertension and glaucoma conditions as set forth in claim 1, wherein said sensor comprises at least one substrate layer manufactured from a material selected from a group including poly(dimethylsiloxane) dialkanol (PDMS), Polyimide, Poly(methyl methacrylate) (PMMA), Parylene, Silicone polyethylene terephthalate (PET) or Polymide (PI).

8. The contact lens embedded sensor system for IOP monitoring in ocular hypertension and glaucoma conditions as set forth in claim 1, wherein said antenna coupled to said sensor is also coupled with eyeglasses.

9. The contact lens embedded sensor system for IOP monitoring in ocular hypertension and glaucoma conditions as set forth in claim 1, wherein said antenna coupled to said sensor is also coupled with a transparent patch headgear.

10. A method of monitoring intraocular pressure (IOP) for glaucoma and ocular hypertension conditions in patients, comprising the steps of:

sensing intraocular pressure (IOP) of a human eye with a contact lens embedded sensor system, the contact lens embedded sensor system comprising a contact lens with a sensor embedded therein, an antenna coupled to said sensor, and an electronic readout circuitry, wherein said sensor comprises at least two resonator type resonator rings, the at least two resonator type resonator rings stacked on top of each other with at least one flexible biocompatible substrate layer sandwiched in between, and wherein said contact lens embedded sensor system is a passive structure;

wherein said electronic readout circuitry comprises an antenna matching hybrid coupler, a power measurement unit and a frequency synthesizer/power amp in parallel, and a microcontroller unit (MCU);

detecting, with the sensor, a resonant frequency shift, when the contact lens comprising the sensor that includes at least two resonator type resonator rings undergoes a change in geometry caused by a change in intraocular pressure (IOP);

performing resonant frequency shift measurements, wherein the antenna coupled to said sensor comprises an antenna loop on a substrate layer measuring said resonant frequency shift;

collecting and processing said resonant frequency shift measurements with the electronic readout circuitry; and interpreting the resonant frequency shift measurements as a change in intraocular pressure (IOP).

11. The method of monitoring intraocular pressure (IOP) for glaucoma and ocular hypertension patients as set forth in claim 10, wherein said electronic readout circuitry comprises different circuitry topologies for one port and two port antenna configurations.

12. The method of monitoring intraocular pressure (IOP) for glaucoma and ocular hypertension patients as set forth in claim 10, wherein collecting and processing said resonant frequency shift measurements with said electronic readout circuitry comprises the steps of:

measuring reflected or transmitted power with said antenna matching hybrid coupler;

scanning, with said a frequency synthesizer controlled by the electronic readout circuitry a frequency range in which the sensor resonates;

collecting, with said power measurement unit, power measurements for each scanned frequency; and digitizing the power measurements by the electronic readout circuitry.

* * * * *